(12) United States Patent
Armstrong et al.

(10) Patent No.: US 10,913,673 B2
(45) Date of Patent: Feb. 9, 2021

(54) COMPOSITIONS FOR MITIGATING HYDROGEN SULFIDE CONTAMINATION USING A RECOMBINANT PROTEIN WITH AN AFFINITY TAG FUSED TO A HYDROGEN SULFIDE SCAVENGING ENZYME

(71) Applicant: BAKER HUGHES, A GE COMPANY, LLC, Houston, TX (US)

(72) Inventors: Charles D. Armstrong, Tomball, TX (US); Frances H. Debenedictis, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 0 days.

(21) Appl. No.: 16/697,915

(22) Filed: Nov. 27, 2019

(65) Prior Publication Data
US 2020/0102238 A1 Apr. 2, 2020

Related U.S. Application Data

(62) Division of application No. 15/639,744, filed on Jun. 30, 2017, now Pat. No. 10,556,815.

(60) Provisional application No. 62/357,025, filed on Jun. 30, 2016.

(51) Int. Cl.
| | | |
|---|---|---|
| *C02F 3/34* | (2006.01) | |
| *B01D 53/52* | (2006.01) | |
| *C02F 1/72* | (2006.01) | |
| *B01D 53/84* | (2006.01) | |
| *C07K 7/06* | (2006.01) | |
| *C07K 14/245* | (2006.01) | |
| *C12N 9/02* | (2006.01) | |
| *C02F 101/10* | (2006.01) | |
| *C02F 103/08* | (2006.01) | |
| *C02F 103/10* | (2006.01) | |

(52) U.S. Cl.
CPC ............ *C02F 3/342* (2013.01); *B01D 53/52* (2013.01); *B01D 53/84* (2013.01); *C02F 1/725* (2013.01); *C07K 7/06* (2013.01); *C07K 14/245* (2013.01); *C12N 9/0051* (2013.01); *C12Y 108/05004* (2013.01); *C02F 2101/101* (2013.01); *C02F 2103/08* (2013.01); *C02F 2103/10* (2013.01); *C07K 2319/20* (2013.01)

(58) Field of Classification Search
None
See application file for complete search history.

(56) References Cited

U.S. PATENT DOCUMENTS

| 8,326,547 | B2 | 12/2012 | Liu et al. | |
|---|---|---|---|---|
| 10,556,815 | B2 * | 2/2020 | Armstrong | B01D 53/84 |
| 2009/0118142 | A1 | 5/2009 | Kuroda et al. | |
| 2014/0134736 | A1 | 5/2014 | Coates | |
| 2015/0083416 | A1 | 3/2015 | Lant et al. | |
| 2016/0030916 | A1 | 2/2016 | Shen et al. | |
| 2016/0039697 | A1 | 2/2016 | Dhulipala et al. | |
| 2016/0160105 | A1 | 6/2016 | Dhulipala et al. | |
| 2016/0369156 | A1 | 12/2016 | Coates | |
| 2017/0137790 | A1 | 5/2017 | Dhulipala et al. | |
| 2017/0216768 | A1 | 8/2017 | Shen et al. | |
| 2018/0002211 | A1 | 1/2018 | Armstrong et al. | |

FOREIGN PATENT DOCUMENTS

| EP | 1953550 | 8/2008 |
|---|---|---|
| WO | 2012/166964 | 12/2012 |
| WO | 2015/042477 | 3/2015 |
| WO | 2016/022367 | 2/2016 |
| WO | 2016/089765 | 6/2016 |
| WO | 2018/006033 | 1/2018 |

OTHER PUBLICATIONS

European Patent Office; PCT International Search Report, Issued in Connection to PCT/US2017/040409; dated Sep. 27, 2017; 6 pages; Europe.
European Patent Office; PCT Written Opinion of the International Searching Authority, Issued in Connection to PCT/US2017/040409; dated Sep. 27, 2017; 10 pages; Europe.
Christoph Griesbeck et al.: "Mechanism of Sulfide-Quinone Reductase Investigated Using Site-Directed Mutagenesis and Sulfur Analysis;" Biochemistry; vol. 41, No. 39; Oct. 1, 2002; pp. 11552-11565; XP055407410; US.
Fuchs Stephen M et al.: "Polyarginine as a multifunctional fusion tag," Protein Science, Wiley, US; vol. 14, No. 6; Jun. 1, 2015; pp. 1538-1544; XP002428590.
Tom Taniguchi et al.: "The Si-tag for immobilizing proteins on a silica surface," Biotechnology and Bioengineering; vol. 96, No. 6; Jan. 1, 2007; pp. 1023-1027; XP055407793.
Abdelhamid Mohamed A A et al: "Application of volcanic ash particles for protein affinity purification with a minimized silica-binding tag," Journal of Bioscience and Bioengineering, Elsevier, Amsterdam, NL; vol. 122, No. 5; May 19, 2016; pp. 633-638; XP029779542.
Wikipedia; Affinity Chromatography; https://en.wikipedia.org/wiki/Affinity_chromatography; Sep. 16, 2017; 6 pages.
Chica et al.; Semi-Rational Approaches to Engineering Enzyme Activity: Combining the Benefits of Directed Evolution and Rational Design; Curr Opin Biotechnol; Aug. 2005; 16(4):378-84.
Singh et al.; Protein Engineering Approaches in the Post-Genomic Era; Curr Protein Pept Sci,; 2017; 18; 1-11.
Accession Q4W5U9; Jul. 5, 2015; Alignment to SEQ ID No. 1; 1 page.
Accession A7ZSK6; Feb. 5, 2018; 2 pages.

* cited by examiner

*Primary Examiner* — Christian L Fronda
(74) *Attorney, Agent, or Firm* — Greenberg Traurig LLP

(57) ABSTRACT

In some embodiments, the present invention provides a recombinant protein comprising an affinity tag configured to attach the recombinant protein to a silicate surface, fused to a hydrogen sulfide scavenging enzyme.

4 Claims, 3 Drawing Sheets
Specification includes a Sequence Listing.

SEQUENCE LISTING

<160> NUMBER OF SEQ ID NOS: 12

<210> SEQ ID NO 1
<211> LENGTH: 456
<212> TYPE: PRT
<213> ORGANISM: Artificial Sequence
<220> FEATURE:
<223> OTHER INFORMATION: Recombinant Protein

<400> SEQUENCE: 1

```
Met Ala His Val Val Ile Leu Gly Gly Thr Gly Gly Met Pro Ala
1               5                   10                  15

Ala Tyr Glu Met Lys Glu Ala Leu Gly Ser Gly His Glu Val Thr Leu
            20                  25                  30

Ile Ser Ala Asn Asp Tyr Phe Gln Phe Val Pro Ser Asn Pro Trp Val
        35                  40                  45

Gly Val Gly Trp Lys Glu Arg Asp Asp Ile Thr Phe Pro Ile Arg His
    50                  55                  60

Tyr Val Glu Arg Lys Gly Ile His Phe Val Ala Gln Ser Ala Glu Arg
65                  70                  75                  80

Ile Asp Ala Glu Ala Gln Asn Ile Thr Leu Ala Asp Gly Ser Thr Val
                85                  90                  95

His Tyr Asp Tyr Leu Met Ile Thr Ala Gly Pro Lys Leu Ala Phe Glu
            100                 105                 110

Asn Val Pro Gly Ser Asp Pro His Glu Gly Pro Val Gln Ser Ile Cys
        115                 120                 125

Thr Val Asp His Ala Glu Arg Ala Phe Ala Glu Tyr Gln Ala Leu Leu
    130                 135                 140

Arg Glu Pro Gly Pro Ile Ala Ile Gly Ala Met Ala Gly Ala Ser Cys
145                 150                 155                 160

Phe Gly Pro Ala Tyr Glu Tyr Ala Met Ile Val Ala Ser Asp Leu Lys
                165                 170                 175

Lys Arg Gly Met Arg Asp Lys Ile Pro Ser Phe Thr Phe Ile Thr Ser
            180                 185                 190

Glu Pro Tyr Leu Gly His Leu Gly Ile Gln Gly Val Gly Asp Ser Lys
        195                 200                 205

Gly Ile Leu Thr Lys Gly Leu Lys Glu Glu Gly Ile Glu Ala Tyr Thr
    210                 215                 220
```

```
Asn Cys Lys Val Thr Lys Val Glu Asp Asn Lys Met Tyr Val Thr Gln
225                 230                 235                 240

Val Asp Glu Lys Gly Glu Thr Ile Lys Glu Met Val Leu Pro Val Lys
            245                 250                 255

Leu Gly Met Met Ile Pro Ala Phe Lys Gly Val Pro Ala Val Ala Gly
        260                 265                 270

Val Glu Gly Leu Cys Asn Pro Gly Gly Phe Val Leu Val Asp Glu His
    275                 280                 285

Gln Arg Ser Lys Lys Tyr Ala Asn Ile Phe Ala Ala Gly Ile Ala Ile
290                 295                 300

Ala Ile Pro Pro Val Glu Thr Thr Pro Val Pro Thr Gly Ala Pro Lys
305                 310                 315                 320

Thr Gly Tyr Met Ile Glu Ser Met Val Ser Ala Ala Val His Asn Ile
                325                 330                 335

Lys Ala Asp Leu Glu Gly Arg Lys Gly Glu Gln Thr Met Gly Thr Trp
            340                 345                 350

Asn Ala Val Cys Phe Ala Asp Met Gly Asp Arg Gly Ala Ala Phe Ile
        355                 360                 365

Ala Leu Pro Gln Leu Lys Pro Arg Lys Val Asp Val Phe Ala Tyr Gly
    370                 375                 380

Arg Trp Val His Leu Ala Lys Val Ala Phe Glu Lys Tyr Phe Ile Arg
385                 390                 395                 400

Lys Met Lys Ile Gly Val Ser Glu Pro Phe Tyr Glu Lys Val Leu Phe
                405                 410                 415

Lys Met Met Gly Ile Thr Arg Leu Lys Glu Glu Asp Ala His Arg Lys
            420                 425                 430

Ala Ser Glu Thr His Ala Asn Asn Ala His Asp Ala Val Ile Asp Arg
        435                 440                 445

Arg Arg Arg Arg Arg Arg Arg
    450                 455

<210> SEQ ID NO 2
<211> LENGTH: 714
<212> TYPE: PRT
<213> ORGANISM: Artificial Sequence
<220> FEATURE:
<223> OTHER INFORMATION: Recombinant Protein

<400> SEQUENCE: 2

Met Ala His Val Val Ile Leu Gly Gly Thr Gly Gly Met Pro Ala
1               5                   10                  15

Ala Tyr Glu Met Lys Glu Ala Leu Gly Ser Gly His Glu Val Thr Leu
                20                  25                  30

Ile Ser Ala Asn Asp Tyr Phe Gln Phe Val Pro Ser Asn Pro Trp Val
            35                  40                  45

Gly Val Gly Trp Lys Glu Arg Asp Asp Ile Thr Phe Pro Ile Arg His
        50                  55                  60

Tyr Val Glu Arg Lys Gly Ile His Phe Val Ala Gln Ser Ala Glu Arg
65                  70                  75                  80

Ile Asp Ala Glu Ala Gln Asn Ile Thr Leu Ala Asp Gly Ser Thr Val
                85                  90                  95

His Tyr Asp Tyr Leu Met Ile Thr Ala Gly Pro Lys Leu Ala Phe Glu
            100                 105                 110

Asn Val Pro Gly Ser Asp Pro His Glu Gly Pro Val Gln Ser Ile Cys
        115                 120                 125
```

```
Thr Val Asp His Ala Glu Arg Ala Phe Ala Glu Tyr Gln Ala Leu Leu
            130                 135                 140

Arg Glu Pro Gly Pro Ile Ala Ile Gly Ala Met Ala Gly Ala Ser Cys
145                 150                 155                 160

Phe Gly Pro Ala Tyr Glu Tyr Ala Met Ile Val Ala Ser Asp Leu Lys
                    165                 170                 175

Lys Arg Gly Met Arg Asp Lys Ile Pro Ser Phe Thr Phe Ile Thr Ser
                180                 185                 190

Glu Pro Tyr Leu Gly His Leu Gly Ile Gln Gly Val Gly Asp Ser Lys
            195                 200                 205

Gly Ile Leu Thr Lys Gly Leu Lys Glu Glu Gly Ile Glu Ala Tyr Thr
210                 215                 220

Asn Cys Lys Val Thr Lys Val Glu Asp Asn Lys Met Tyr Val Thr Gln
225                 230                 235                 240

Val Asp Glu Lys Gly Glu Thr Ile Lys Glu Met Val Leu Pro Val Lys
                245                 250                 255

Leu Gly Met Met Ile Pro Ala Phe Lys Gly Val Pro Ala Val Ala Gly
            260                 265                 270

Val Glu Gly Leu Cys Asn Pro Gly Gly Phe Val Leu Val Asp Glu His
        275                 280                 285

Gln Arg Ser Lys Lys Tyr Ala Asn Ile Phe Ala Ala Gly Ile Ala Ile
290                 295                 300

Ala Ile Pro Pro Val Glu Thr Thr Pro Val Pro Thr Gly Ala Pro Lys
305                 310                 315                 320

Thr Gly Tyr Met Ile Glu Ser Met Val Ser Ala Ala Val His Asn Ile
                325                 330                 335

Lys Ala Asp Leu Glu Gly Arg Lys Gly Glu Gln Thr Met Gly Thr Trp
            340                 345                 350

Asn Ala Val Cys Phe Ala Asp Met Gly Asp Arg Gly Ala Ala Phe Ile
            355                 360                 365

Ala Leu Pro Gln Leu Lys Pro Arg Lys Val Asp Val Phe Ala Tyr Gly
370                 375                 380

Arg Trp Val His Leu Ala Lys Val Ala Phe Glu Lys Tyr Phe Ile Arg
385                 390                 395                 400

Lys Met Lys Ile Gly Val Ser Glu Pro Phe Tyr Glu Lys Val Leu Phe
                405                 410                 415

Lys Met Met Gly Ile Thr Arg Leu Lys Glu Glu Asp Ala His Arg Lys
            420                 425                 430

Ala Ser Glu Thr His Ala Asn Asn Ala His Ala Val Val Lys Cys Lys
            435                 440                 445

Pro Thr Ser Pro Gly Arg Arg His Val Val Lys Val Asn Pro Glu
450                 455                 460

Leu His Lys Gly Lys Pro Phe Ala Pro Leu Leu Glu Lys Asn Ser Lys
465                 470                 475                 480

Ser Gly Gly Arg Asn Asn Asn Gly Arg Ile Thr Thr Arg His Ile Gly
                485                 490                 495

Gly Gly His Lys Gln Ala Tyr Arg Ile Val Asp Phe Lys Arg Asn Lys
            500                 505                 510

Asp Gly Ile Pro Ala Val Val Glu Arg Leu Glu Tyr Asp Pro Asn Arg
            515                 520                 525

Ser Ala Asn Ile Ala Leu Val Leu Tyr Lys Asp Gly Glu Arg Arg Tyr
530                 535                 540
```

-continued

Ile Leu Ala Pro Lys Gly Leu Lys Ala Gly Asp Gln Ile Gln Ser Gly
545                 550                 555                 560

Val Asp Ala Ala Ile Lys Pro Gly Asn Thr Leu Pro Met Arg Asn Ile
                565                 570                 575

Pro Val Gly Ser Thr Val His Asn Val Glu Met Lys Pro Gly Lys Gly
            580                 585                 590

Gly Gln Leu Ala Arg Ser Ala Gly Thr Tyr Val Gln Ile Val Ala Arg
        595                 600                 605

Asp Gly Ala Tyr Val Thr Leu Arg Leu Arg Ser Gly Glu Met Arg Lys
    610                 615                 620

Val Glu Ala Asp Cys Arg Ala Thr Leu Gly Glu Val Gly Asn Ala Glu
625                 630                 635                 640

His Met Leu Arg Val Leu Gly Lys Ala Gly Ala Arg Trp Arg Gly
                645                 650                 655

Val Arg Pro Thr Val Arg Gly Thr Ala Met Asn Pro Val Asp His Pro
                660                 665                 670

Gly Gly Gly His Glu Gly Arg Asn Phe Gly Lys His Pro Val Thr Pro
            675                 680                 685

Trp Gly Val Gln Thr Lys Gly Lys Lys Thr Arg Ser Asn Lys Arg Thr
690                 695                 700

Asp Lys Phe Ile Val Arg Arg Arg Ser Lys
705                 710

<210> SEQ ID NO 3
<211> LENGTH: 9
<212> TYPE: PRT
<213> ORGANISM: Artificial Sequence
<220> FEATURE:
<223> OTHER INFORMATION: Affinity Tag

<400> SEQUENCE: 3

Arg Arg Arg Arg Arg Arg Arg Arg Arg
1               5

<210> SEQ ID NO 4
<211> LENGTH: 272
<212> TYPE: PRT
<213> ORGANISM: Artificial Sequence
<220> FEATURE:
<223> OTHER INFORMATION: Affinity Tag

<400> SEQUENCE: 4

Ala Val Val Lys Cys Lys Pro Thr Ser Pro Gly Arg Arg His Val Val
1               5                   10                  15

Lys Val Val Asn Pro Glu Leu His Lys Gly Lys Pro Phe Ala Pro Leu
                20                  25                  30

Leu Glu Lys Asn Ser Lys Ser Gly Gly Arg Asn Asn Asn Gly Arg Ile
            35                  40                  45

Thr Thr Arg His Ile Gly Gly Gly His Lys Gln Ala Tyr Arg Ile Val
        50                  55                  60

Asp Phe Lys Arg Asn Lys Asp Gly Ile Pro Ala Val Val Glu Arg Leu
65                  70                  75                  80

Glu Tyr Asp Pro Asn Arg Ser Ala Asn Ile Ala Leu Val Leu Tyr Lys
                85                  90                  95

Asp Gly Glu Arg Arg Tyr Ile Leu Ala Pro Lys Gly Leu Lys Ala Gly
            100                 105                 110

Asp Gln Ile Gln Ser Gly Val Asp Ala Ala Ile Lys Pro Gly Asn Thr
        115                 120                 125

Leu Pro Met Arg Asn Ile Pro Val Gly Ser Thr Val His Asn Val Glu
        130                 135                 140

Met Lys Pro Gly Lys Gly Gln Leu Ala Arg Ser Ala Gly Thr Tyr
145                 150                 155                 160

Val Gln Ile Val Ala Arg Asp Gly Ala Tyr Val Thr Leu Arg Leu Arg
                165                 170                 175

Ser Gly Glu Met Arg Lys Val Glu Ala Asp Cys Arg Ala Thr Leu Gly
            180                 185                 190

Glu Val Gly Asn Ala Glu His Met Leu Arg Val Leu Gly Lys Ala Gly
        195                 200                 205

Ala Ala Arg Trp Arg Gly Val Arg Pro Thr Val Arg Gly Thr Ala Met
    210                 215                 220

Asn Pro Val Asp His Pro Gly Gly His Glu Gly Arg Asn Phe Gly
225                 230                 235                 240

Lys His Pro Val Thr Pro Trp Gly Val Gln Thr Lys Gly Lys Lys Thr
                245                 250                 255

Arg Ser Asn Lys Arg Thr Asp Lys Phe Ile Val Arg Arg Ser Lys
            260                 265                 270

<210> SEQ ID NO 5
<211> LENGTH: 786
<212> TYPE: DNA
<213> ORGANISM: Artificial Sequence
<220> FEATURE:
<223> OTHER INFORMATION: Recombinant Construct

<400> SEQUENCE: 5
catatggtga gcaaaggcga agaactgttt accggcgtgg tgccgattct ggtggaactg      60
gatggcgatg tgaacggcca taaatttagc gtgagcggcg aaggcgaagg cgatgcgacc     120
tatggcaaac tgaccctgaa atttatttgc accaccggca aactgccggt gccgtggccg     180
accctggtga ccaccctgac ctatggcgtg cagtgcttta gccgctatcc ggatcatatg     240
aaacagcatg attttttta aagcgcgatg ccggaaggct atgtgcagga acgcaccatt     300
ttttttaaag atgatggcaa ctataaaacc cgcgcggaag tgaaatttga aggcgatacc     360
ctggtgaacc gcattgaact gaaaggcatt gattttaaag aagatggcaa cattctgggc     420
cataaactgg aatataacta taacagccat aacgtgtata ttatggcgga taaacagaaa     480
aacggcatta agtgaacttt aaaattcgc cataacattg aagatggcag cgtgcagctg     540
gcggatcatt atcagcagaa cacccccgatt ggcgatggcc cggtgctgct gccggataac     600
cattatctga gcacccagag cgcgctgagc aaagatccga cgaaaaacg cgatcatatg     660
gtgctgctgg aatttgtgac cgcggcgggc attaccctgg gcatggatga actgtataaa     720
gatgatgatg ataaagatgc ggtgattgat cgccgccgcc gccgccgccg ccgccgctga     780
ggatcc                                                              786

<210> SEQ ID NO 6
<211> LENGTH: 108
<212> TYPE: PRT
<213> ORGANISM: Artificial Sequence
<220> FEATURE:
<223> OTHER INFORMATION: Recombinant Protein

<400> SEQUENCE: 6

Ile Met Ala Asp Lys Gln Lys Asn Gly Ile Lys Val Asn Phe Lys Ile
1               5                   10                  15

```
Arg His Asn Ile Glu Asp Gly Ser Val Gln Leu Ala Asp His Tyr Gln
             20                  25                  30

Gln Asn Thr Pro Ile Gly Asp Gly Pro Val Leu Leu Pro Asp Asn His
         35                  40                  45

Tyr Leu Ser Thr Gln Ser Ala Leu Ser Lys Asp Pro Asn Glu Lys Arg
 50                  55                  60

Asp His Met Val Leu Leu Glu Phe Val Thr Ala Ala Gly Ile Thr Leu
 65                  70                  75                  80

Gly Met Asp Glu Leu Tyr Lys Asp Asp Asp Lys Asp Ala Val Ile
             85                  90                  95

Asp Arg Arg Arg Arg Arg Arg Arg Arg Gly Ser
            100                 105
```

<210> SEQ ID NO 7
<211> LENGTH: 2154
<212> TYPE: DNA
<213> ORGANISM: Artificial Sequence
<220> FEATURE:
<223> OTHER INFORMATION: Recombinant Construct

<400> SEQUENCE: 7

```
catatggcgc atgtggtgat tctgggcggc ggcaccggcg gcatgccggc ggcgtatgaa      60
atgaaagaag cgctgggcag cggccatgaa gtgaccctga ttagcgcgaa cgattatttt     120
cagtttgtgc cgagcaaccc gtgggtgggc gtgggctgga agaacgcga tgatattacc      180
tttccgattc gccattatgt ggaacgcaaa ggcattcatt tgtggcgca gagcgcggaa      240
cgcattgatg cggaagcgca gaacattacc ctggcggatg cagcaccgt gcattatgat     300
tatctgatga ttaccgcggg cccgaaactg gcgtttgaaa acgtgccggg cagcgatccg     360
catgaaggcc cggtgcagag catttgcacc gtggatcatg cggaacgcgc gtttgcggaa     420
tatcaggcgc tgctgcgcga accgggcccg attgcgattg gcgcgatggc gggcgcgagc     480
tgctttggcc ggcgtatga atatgcgatg attgtggcga cgatctgaa aaaacgcggc      540
atgcgcgata aaattccgag ctttaccttt attaccagcg aaccgtatct gggccatctg     600
ggcattcagg gcgtgggcga tagcaaaggc attctgacca aaggcctgaa agaagaaggc     660
attgaagcgt ataccaactg caaagtgacc aaagtggaag ataacaaaat gtatgtgacc     720
caggtggatg aaaaaggcga aaccattaaa gaaatggtgc tgccggtgaa actgggcatg     780
atgattccgg cgtttaaagg cgtgccggcg gtggcgggcg tggaaggcct gtgcaacccg     840
ggcggctttg tgctggtgga tgaacatcag cgcagcaaaa aatatgcgaa catttttgcg     900
gcgggcattg cgattgcgat tccgccggtg aaaccaccc cggtgccgac cggcgcgccg     960
aaaaccggct atatgattga agcatggtg agcgcggcgg tgcataacat taaagcggat    1020
ctggaaggcc gcaaaggcga acagaccatg gcacctgga acgcggtgtg ctttgcggat    1080
atgggcgatc gcggcgcggc gtttattgcg ctgccgcagc tgaaaccgcg caaagtggat    1140
gtgtttgcgt atggccgctg ggtgcatctg gcgaaagtgg cgtttgaaaa atatttttatt   1200
cgcaaaatga aaattggcgt gagcgaaccg ttttatgaaa aagtgctgtt taaatgatg     1260
ggcattaccc gcctgaaaga agaagatgcg catcgcaaag cgagcgaaac ccatgcgaac    1320
aacgcgcatg cggtggtgaa atgcaaaccg accagcccgg ccgccgcca tgtggtgaaa    1380
gtggtgaacc cggaactgca taaggcaaa ccgtttgcgc cgctgctgga aaaaacagc      1440
aaaagcggcg gccgcaacaa caacggccgc attaccaccc gccatattgg cggcggccat   1500
aaacaggcgt atcgcattgt ggatttttaaa cgcaacaaag atggcattcc ggcggtggtg    1560
```

-continued

```
gaacgcctgg aatatgatcc gaaccgcagc gcgaacattg cgctggtgct gtataaagat   1620
ggcgaacgcc gctatattct ggcgccgaaa ggcctgaaag cgggcgatca gattcagagc   1680
ggcgtggatg cggcgattaa accgggcaac accctgccga tgcgcaacat tccggtgggc   1740
agcaccgtgc ataacgtgga aatgaaaccg ggcaaaggcg ccagctggc gcgcagcgcg    1800 ggcacctatg tgcagattgt ggcgcgcgat ggcgcgtatg tgaccctgcg cctgcgcagc   1860
ggcgaaatgc gcaaagtgga agcggattgc cgcgcgaccc tgggcgaagt gggcaacgcg   1920
gaacatatgc tgcgcgtgct gggcaaagcg ggcgcggcgc gctggcgcgg cgtgcgcccg   1980
accgtgcgcg gcaccgcgat gaacccggtg gatcatccgg cggcggccat gaaggccgc    2040 aactttggca acatccggt gaccccgtgg ggcgtgcaga ccaaaggcaa aaaacccgc     2100 agcaacaaac gcaccgataa atttattgtg cgccgccgca gcaaatgagg atcc          2154
```

<210> SEQ ID NO 8
<211> LENGTH: 435
<212> TYPE: PRT
<213> ORGANISM: Artificial Sequence
<220> FEATURE:
<223> OTHER INFORMATION: Recombinant Protein

<400> SEQUENCE: 8

```
Met Ala His Val Val Ile Leu Gly Ala Gly Thr Gly Gly Met Pro Ala
1               5                   10                  15

Ala Tyr Glu Met Lys Glu Ala Leu Gly Ser Gly His Glu Val Thr Leu
            20                  25                  30

Ile Ser Ala Asn Asp Tyr Phe Gln Phe Val Pro Ser Asn Pro Trp Val
        35                  40                  45

Gly Val Gly Trp Thr Lys Arg Asp Asp Ile Ala Phe Pro Ile Lys Pro
    50                  55                  60

Tyr Val Glu Arg Lys Gly Ile His Phe Ile Pro Lys Ala Ala Glu Lys
65                  70                  75                  80

Ile Asp Ala Glu Gly Gln Glu Ile Thr Leu Ala Asp Gly Ser Lys Val
                85                  90                  95

Arg Tyr Asp Tyr Leu Leu Ile Thr Thr Gly Pro Lys Leu Ala Phe Glu
            100                 105                 110

Asn Val Pro Gly Ser Asp Pro His Glu Gly Pro Ile Gln Ser Ile Cys
        115                 120                 125

Thr Val Asp His Ala Glu Lys Ala Tyr His Asp Tyr Gln Ala Leu Leu
    130                 135                 140

Ala Glu Pro Gly Pro Ile Val Ile Gly Ala Met Gly Gly Ala Ser Cys
145                 150                 155                 160

Phe Gly Pro Ala Tyr Glu Tyr Ala Met Val Val Ala Ser Asp Leu Lys
                165                 170                 175

Lys Arg Gly Met Arg Asp Lys Ile Ser Ser Phe Thr Phe Val Thr Ser
            180                 185                 190

Glu Pro Tyr Leu Gly His Leu Gly Ile Gln Gly Val Gly Asp Ser Thr
        195                 200                 205

Gly Ile Leu Ser Lys Gly Leu Lys Glu Glu Gly Ile Glu Ala Tyr Thr
    210                 215                 220

Asn Cys Lys Val Thr Lys Val Glu Gly Gly Lys Met Phe Val Thr Gln
225                 230                 235                 240

Val Asn Asp Lys Gly Glu Val Ala Lys Glu Phe Thr Leu Pro Val Lys
                245                 250                 255
```

Phe Gly Met Met Ile Pro Ala Phe Lys Gly Val Pro Ala Val Ala Gly
                260                 265                 270

Val Glu Gly Leu Cys Asn Pro Gly Phe Val Leu Val Asp Glu His
            275                 280                 285

Gln Arg Ser Lys Lys Tyr Ala Asn Ile Phe Ala Ala Gly Ile Ala Ile
        290                 295                 300

Ala Ile Pro Pro Val Glu Ala Thr Pro Val Pro Thr Gly Ala Pro Lys
305                 310                 315                 320

Thr Gly Tyr Met Ile Glu Ser Met Val Ser Ala Ala Val His Asn Ile
                325                 330                 335

Lys Ala Asp Leu Glu Gly Arg Lys Gly Glu Gln Thr Met Gly Thr Trp
            340                 345                 350

Asn Ala Val Cys Phe Ala Asp Met Gly Asp Arg Gly Ala Ala Phe Val
        355                 360                 365

Ala Leu Pro Gln Leu Arg Pro Arg Lys Val Asp Val Phe Ala Tyr Gly
370                 375                 380

Arg Trp Val His Leu Ala Lys Val Ala Phe Glu Lys Tyr Phe Ile Arg
385                 390                 395                 400

Lys Met Lys Met Gly Val Ser Glu Pro Phe Tyr Glu Lys Val Leu Phe
                405                 410                 415

Lys Met Met Gly Ile Thr Arg Leu Lys Glu Glu Val Pro Pro His Arg
            420                 425                 430

Lys Ala Ser
        435

<210> SEQ ID NO 9
<211> LENGTH: 435
<212> TYPE: PRT
<213> ORGANISM: Artificial Sequence
<220> FEATURE:
<223> OTHER INFORMATION: Recombinant Protein

<400> SEQUENCE: 9

Met Ala His Val Val Ile Leu Gly Ala Gly Thr Gly Met Pro Ala
1               5                   10                  15

Ala Tyr Glu Met Lys Glu Ala Leu Gly Ser Gly His Glu Val Thr Leu
            20                  25                  30

Ile Ser Ala Asn Asp Tyr Phe Gln Phe Val Pro Ser Asn Pro Trp Val
        35                  40                  45

Gly Val Gly Trp Thr Lys Arg Asp Asp Ile Ala Phe Pro Ile Lys Pro
    50                  55                  60

Tyr Val Glu Arg Lys Gly Ile His Phe Ile Pro Lys Ala Ala Glu Lys
65                  70                  75                  80

Ile Asp Ala Glu Gly Gln Glu Ile Thr Leu Ala Asp Gly Ser Lys Val
                85                  90                  95

Arg Tyr Asp Tyr Leu Leu Ile Thr Thr Gly Pro Lys Leu Ala Phe Glu
            100                 105                 110

Asn Val Pro Gly Ser Asp Pro His Glu Gly Pro Ile Gln Ser Ile Cys
        115                 120                 125

Thr Val Asp His Ala Glu Lys Ala Tyr His Asp Tyr Gln Ala Leu Leu
    130                 135                 140

Ala Glu Pro Gly Pro Ile Val Ile Gly Ala Met Gly Gly Ala Ser Cys
145                 150                 155                 160

Phe Gly Pro Ala Tyr Glu Tyr Ala Met Val Val Ala Ser Asp Leu Lys
                165                 170                 175

-continued

Lys Arg Gly Met Arg Asp Lys Ile Ser Ser Phe Thr Phe Val Thr Ser
            180                 185                 190

Glu Pro Tyr Leu Gly His Leu Gly Ile Gln Gly Val Gly Asp Ser Thr
        195                 200                 205

Gly Ile Leu Ser Lys Gly Leu Lys Glu Glu Gly Ile Glu Ala Tyr Thr
    210                 215                 220

Asn Cys Lys Val Thr Lys Val Glu Gly Gly Lys Met Phe Val Thr Gln
225                 230                 235                 240

Val Asn Asp Lys Gly Glu Val Ala Lys Glu Phe Thr Leu Pro Val Lys
                245                 250                 255

Phe Gly Met Met Ile Pro Ala Phe Lys Gly Val Pro Ala Val Ala Gly
            260                 265                 270

Val Glu Gly Leu Cys Asn Pro Gly Gly Phe Val Leu Val Asp Glu His
        275                 280                 285

Gln Arg Ser Lys Lys Tyr Ala Asn Ile Phe Ala Ala Gly Ile Ala Ile
    290                 295                 300

Ala Ile Pro Pro Val Glu Ala Thr Pro Val Pro Thr Gly Ala Pro Lys
305                 310                 315                 320

Thr Gly Tyr Met Ile Glu Ser Met Val Ser Ala Ala Val His Asn Ile
                325                 330                 335

Lys Ala Asp Leu Glu Gly Arg Lys Gly Glu Gln Thr Met Gly Thr Trp
            340                 345                 350

Asn Ala Val Cys Phe Ala Asp Met Gly Asp Arg Gly Ala Ala Phe Val
        355                 360                 365

Ala Leu Pro Gln Leu Arg Pro Arg Lys Val Asp Val Phe Ala Tyr Gly
    370                 375                 380

Arg Trp Val His Leu Ala Lys Val Ala Phe Glu Lys Tyr Phe Ile Arg
385                 390                 395                 400

Lys Met Lys Met Gly Val Ser Glu Pro Phe Tyr Gln Lys Val Leu Phe
                405                 410                 415

Lys Met Met Gly Ile Thr Arg Leu Lys Glu Val Pro Pro His Arg
            420                 425                 430

Lys Ala Ser
        435

<210> SEQ ID NO 10
<211> LENGTH: 422
<212> TYPE: PRT
<213> ORGANISM: Artificial Sequence
<220> FEATURE:
<223> OTHER INFORMATION: Recombinant Protein

<400> SEQUENCE: 10

Met Ala His Val Val Leu Gly Ala Gly Thr Gly Gly Met Pro Cys
1               5                   10                  15

Ala Tyr Glu Leu Arg Ala Glu Leu Gly Arg Glu His Glu Val Thr Met
                20                  25                  30

Ile Asn Glu Arg Glu Tyr Phe Gln Phe Val Pro Ser Asn Pro Trp Leu
            35                  40                  45

Ala Val Gly Trp Arg Asp Arg Ser His Ile Thr Phe Asp Ile Arg Pro
        50                  55                  60

His Leu Glu Arg Lys Gly Ile Asn Phe Ile Ala Lys Arg Val Asp Lys
65                  70                  75                  80

Ile Asp Ala Glu Gly Asn Lys Leu Glu Leu Asp Asp Gly Glu Thr Ile
                85                  90                  95

Glu Tyr Asp Tyr Leu Val Ile Ala Thr Gly Pro Arg Leu Ala Phe Glu
                100                 105                 110

Glu Val Glu Gly Ser Gly Pro Glu Gly His Thr Gln Ser Ile Cys Thr
            115                 120                 125

Val Asn His Ala Glu Lys Ala Phe Asp Ala Tyr Lys Asp Leu Leu Asp
        130                 135                 140

Glu Pro Gly Pro Val Ile Ile Gly Ala Met Pro Phe Ala Ser Cys Phe
145                 150                 155                 160

Gly Pro Ala Tyr Glu Phe Ser Phe Ile Met Asp Ser Asp Leu Arg Lys
                165                 170                 175

Arg Lys Met Arg Asp Lys Val Pro Met Thr Tyr Val Thr Ser Glu Pro
            180                 185                 190

Tyr Ile Gly His Leu Gly Leu Gly Val Gly Asp Ser Lys Gly Phe
        195                 200                 205

Leu Glu Ser Asp Phe Arg Ala His His Ile Asn Trp Ile Thr Asn Ala
    210                 215                 220

Lys Val Ile Lys Val Glu Ala Gly Lys Met Phe Val Glu Gln Tyr Asp
225                 230                 235                 240

Asp Ser Gly His Lys Ile Lys Glu His Glu Leu Glu Phe Lys Tyr Ser
                245                 250                 255

Met Met Leu Pro Ala Phe Lys Gly Val Asp Ala Val Ala Asn Val Glu
            260                 265                 270

Gly Leu Cys Asn Pro Arg Gly Phe Val Phe Val Asp His Gln Cys
        275                 280                 285

Asn Pro Thr Tyr Lys Asn Ile Tyr Ala Ala Gly Val Cys Ile Ala Ile
    290                 295                 300

Pro Pro Val Glu Ala Thr Ala Val Pro Thr Gly Ala Pro Lys Thr Gly
305                 310                 315                 320

Tyr Met Ile Glu Ser Met Val Thr Ala Ile Val His Asn Ile Ala Asp
                325                 330                 335

Asp Leu Ala Gly Lys Glu Gly Thr Thr Leu Ala Thr Trp Asn Ala Ile
            340                 345                 350

Cys Leu Ala Asp Met Gly Asp Thr Gly Ala Ala Phe Val Ala Leu Pro
        355                 360                 365

Gln Ile Pro Pro Arg Asn Val Ala Trp Phe Lys Lys Gly Lys Trp Val
    370                 375                 380

His Met Ala Lys Ile Ala Phe Glu Lys Tyr Phe Ile Arg Lys Met Lys
385                 390                 395                 400

Lys Gly Thr Ser Glu Pro Ile Tyr Glu Lys Tyr Ile Leu Lys Met Leu
                405                 410                 415

Gly Ile Gly Lys Leu Lys
            420

<210> SEQ ID NO 11
<211> LENGTH: 429
<212> TYPE: PRT
<213> ORGANISM: Artificial Sequence
<220> FEATURE:
<223> OTHER INFORMATION: Recombinant Protein

<400> SEQUENCE: 11

Met Ala His Ile Val Val Ile Gly Ala Gly Ile Gly Gly Met Pro Ala
1               5                   10                  15

Ala Tyr Glu Leu Arg Ser Lys Leu Pro Ala Gln His Arg Val Thr Val
            20                  25                  30

Ile Ser Ala Val Asp Tyr Phe His Phe Val Pro Ser Asn Pro Trp Ile
            35                  40                  45

Ala Val Gly Trp Arg Gln Arg Glu Asp Ile Val Leu Gln Leu Ala Pro
 50                  55                  60

Leu Leu Gln Arg Lys Gly Ile Asp Phe Ile Ala Ser Pro Val Gln Thr
 65                  70                  75                  80

Ile Asp Ala Ala Gly Asn Ser Leu Ala Leu Ala Asn Gly Gln Thr Val
                 85                  90                  95

Ala Tyr Asp Tyr Leu Val Ile Thr Thr Gly Pro Arg Leu Ala Phe Glu
            100                 105                 110

Glu Val Pro Gly Ala Gly Pro Ile Asp Gly His Thr His Ser Ile Cys
            115                 120                 125

Thr Val Asp His Ala Gln His Phe Trp Ala Asp Tyr Glu Lys Phe Leu
130                 135                 140

Glu Asn Pro Gly Pro Met Val Ile Gly Ala Met Pro Gly Ala Ser Cys
145                 150                 155                 160

Phe Gly Pro Ala Tyr Glu Phe Ala Phe Ile Val Ser Ala Asp Leu Arg
                165                 170                 175

Lys Arg Lys Leu Arg His Lys Val Pro Leu Thr Tyr Val Thr Ser Glu
            180                 185                 190

Pro Tyr Ile Gly His Leu Gly Leu Gly Gly Val Gly Asp Ser Lys Ser
            195                 200                 205

Met Leu Glu Ser Glu Leu Arg Gly Gln Asp Ile Lys Trp Ile Thr Asn
            210                 215                 220

Ala Lys Thr Thr Arg Val Glu Asp Gly Lys Met Met Val Asp Gln Leu
225                 230                 235                 240

Asp Asp Gln Gly Lys Leu Leu Lys Gln His Glu Leu Pro Phe Lys Leu
                245                 250                 255

Ser Met Met Leu Pro Ala Phe Lys Gly Val Asp Ala Val Ala Ala Val
            260                 265                 270

Pro Ser Leu Cys Asn Pro Arg Gly Phe Val Leu Ile Asp Ala His Gln
            275                 280                 285

Arg Ser Lys Ala Tyr Pro Asn Ile Phe Ala Ala Gly Val Cys Val Ala
290                 295                 300

Ile Pro Pro Val Glu Val Thr Pro Val Pro Thr Gly Ala Pro Lys Thr
305                 310                 315                 320

Gly Tyr Met Ile Glu Thr Met Val Ser Ala Ile Val His Asn Ile Ala
                325                 330                 335

Ala Asp Leu Glu Gly Lys Pro Ala Thr Ala Thr Ala Thr Trp Asn Ala
            340                 345                 350

Ile Cys Leu Ala Asp Met Gly Asp Thr Gly Ala Ala Phe Val Ala Leu
            355                 360                 365

Pro Gln Ile Pro Pro Arg Asn Val Asn Trp Phe Lys Lys Gly Lys Trp
            370                 375                 380

Val His Leu Gly Lys Ile Ala Phe Glu Lys Tyr Phe Leu Gly Lys Ile
385                 390                 395                 400

Lys Ser Gly Asn Thr Asp Pro Ile Tyr Glu Lys Tyr Val Leu Lys Ile
                405                 410                 415

Leu Gly Ile Glu Arg Leu Pro Glu Pro Ser Gly Pro Arg
            420                 425

<210> SEQ ID NO 12
<211> LENGTH: 423
<212> TYPE: PRT

<213> ORGANISM: Artificial Sequence
<220> FEATURE:
<223> OTHER INFORMATION: Recombinant Protein

<400> SEQUENCE: 12

```
Met Ala His Ile Val Ile Leu Gly Ala Gly Thr Gly Gly Met Pro Ala
1               5                   10                  15

Ala Tyr Glu Met Lys Glu Met Leu Gly Lys Gly His Glu Val Thr Val
            20                  25                  30

Val Asn Glu Arg Asp Tyr Phe Gln Phe Val Pro Ser Asn Pro Trp Val
        35                  40                  45

Ala Val Gly Trp Arg Thr Arg Ser Asp Ile Thr Phe Pro Ile Glu Lys
    50                  55                  60

Tyr Leu Ser Lys Lys Asp Ile Lys Phe Ile Cys Ser Arg Cys Glu Lys
65                  70                  75                  80

Ile Asp Ala Glu Gly Asn Ala Leu His Leu Ala Asp Gly Gln Ile Val
                85                  90                  95

Lys Tyr Asp Tyr Leu Val Ile Ala Thr Gly Pro Lys Leu Phe Phe Gln
            100                 105                 110

Glu Val Glu Gly Ala Gly Pro His Gly His Thr His Ser Val Cys
        115                 120                 125

Asp Val Thr His Ala Glu Gly Ala Tyr Ala Asp Tyr Gln Lys Leu Leu
    130                 135                 140

Ala Lys Gly Ser Gly His Ile Ile Val Gly Ala Met Pro Phe Ala Ser
145                 150                 155                 160

Cys Phe Gly Pro Ala Tyr Glu Phe Ala Phe Ile Val Asp Ala Asp Leu
                165                 170                 175

Arg Lys Arg Gly Leu Arg His Lys Phe Lys Met Thr Tyr Val Ser Ser
            180                 185                 190

Glu Pro Tyr Ile Gly His Leu Gly Leu Gly Gly Val Gly Asp Ser Lys
        195                 200                 205

Gly Met Leu Glu Ser Glu Leu Arg Asn His His Met Gly Trp Ile Thr
    210                 215                 220

Asn Ala Lys Thr Thr Lys Val Glu Ala Gly Lys Met His Val Thr Glu
225                 230                 235                 240

Met Thr Ala Lys Gly Glu Val Glu Lys Glu His Val Ile Asp Phe Asp
                245                 250                 255

Met Ala Met Met Leu Pro Ala Phe Lys Gly Val Asp Ala Val Ala Ala
            260                 265                 270

Val Glu Gly Leu Cys Asn Pro Arg Gly Phe Val Ile Val Asp Glu Leu
        275                 280                 285

His Arg Ser Pro Lys Tyr Lys Asn Ile Tyr Ser Ala Gly Val Cys Ile
    290                 295                 300

Ala Ile Pro Pro Val Glu Ala Thr Pro Val Pro Thr Gly Ala Pro Lys
305                 310                 315                 320

Thr Gly Tyr Met Ile Glu Ser Met Val Thr Ser Leu Val His Asn Ile
                325                 330                 335

Ala Asp Glu Leu Ala Gly Lys Glu Pro His Thr Thr Ala Thr Trp Asn
            340                 345                 350

Ala Ile Cys Leu Ala Asp Met Gly Asp Thr Gly Ala Ala Phe Val Ala
        355                 360                 365

Leu Pro Gln Ile Pro Pro Arg Asn Val Ala Trp Phe Lys Lys Gly Lys
    370                 375                 380

Trp Val His Met Ala Lys Ile Ala Phe Glu Lys Tyr Phe Ile Arg Lys
```

-continued

```
              385                 390                 395                 400
Met Lys Lys Gly Ser Ser Glu Pro Phe Tyr Glu Lys Ser Ile Leu Lys
                        405                 410                 415
Met Met Gly Ile Thr Arg Ile
                420
```

COMPOSITIONS FOR MITIGATING HYDROGEN SULFIDE CONTAMINATION USING A RECOMBINANT PROTEIN WITH AN AFFINITY TAG FUSED TO A HYDROGEN SULFIDE SCAVENGING ENZYME

RELATED APPLICATIONS

This application is a divisional application and claims the benefit, and priority benefit, of U.S. patent application Ser. No. 15/639,744, filed Jun. 30, 2017, which claims the benefit and priority benefit of U.S. Provisional Patent Application Ser. No. 62/357,025, filed Jun. 30, 2016; entitled "COMPOSITIONS AND METHODS FOR MITIGATING HYDROGEN SULFIDE CONTAMINATION," the contents of each are incorporated by reference herein in their entirety.

TECHNICAL FIELD

In some embodiments, the present invention is related to compositions and methods for attaching proteins to silicate surfaces. In particular, in some embodiments, the present invention is related to compositions and methods for mitigating hydrogen sulfide and/or mercaptan contamination of a liquid within a reservoir using an enzyme attached to the silicate surface of a reservoir.

BACKGROUND

Hydrogen sulfide and mercaptans are present in underground water removed with crude oil, in crude oil itself, in natural gases and in gases associated with underground water and crude oil. Hydrogen sulfide and mercaptans are characterized by highly noxious odors and typically are highly corrosive. Uncontrolled emissions of hydrogen sulfide give rise to severe health hazards. The presence of hydrogen sulfide and mercaptans is further objectionable because they often react with desirable hydrocarbons as well as fuel system components.

SUMMARY OF INVENTION

In one embodiment, the present invention provides a recombinant protein comprising an affinity tag configured to attach the recombinant protein to a silicate surface, fused to a hydrogen sulfide scavenging enzyme.

In one embodiment, the affinity tag configured to attach the recombinant protein to a silicate surface is nonarginine (i.e., non-, meaning nine, arginine residues: RRRRRRRRR).

In one embodiment, the affinity tag configured to attach the recombinant protein to a silicate surface is the 30 kDa L2 protein from the E. Coli 50S ribosomal subunit.

In one embodiment, the hydrogen sulfide scavenging enzyme is sulfide quinone reductase.

In one embodiment, the sulfide quinone reductase is derived from Acidophilus ferroxidans.

In one embodiment, the recombinant protein comprising an affinity tag configured to attach the recombinant protein to a silicate surface, fused to a hydrogen sulfide scavenging enzyme comprises the protein having the amino acid sequence set forth in SEQ ID. No: 1. The recombinant protein is referred to herein as "SQR-$R_9$".

In one embodiment, the recombinant protein comprises the protein having the amino acid sequence set forth in SEQ ID. No: 1.

In one embodiment, the recombinant protein comprising an affinity tag configured to attach the recombinant protein to a silicate surface, fused to a hydrogen sulfide scavenging enzyme comprises the protein having the amino acid sequence set forth in SEQ ID. No: 2. The recombinant protein is referred to herein as "SQR-L2".

In one embodiment, the recombinant protein comprises the protein having the amino acid sequence set forth in SEQ ID. No: 2.

In one embodiment, the affinity tag is the peptide having the amino acid sequence set forth in SEQ ID. No: 3.

In one embodiment, the affinity tag is the peptide having the amino acid sequence set forth in SEQ ID. No: 4.

In one embodiment, the present invention provides a method, wherein the method scavenges hydrogen sulfide and/or mercaptans from a liquid within a reservoir defined by a solid silicate surface, the method comprising contacting the solid silicate surface with a catalytically effective amount of the recombinant protein according to some embodiments of the present invention, wherein the recombinant protein catalyzes the oxidation of the hydrogen sulfide and/or mercaptans to a sulfur containing oxidation product.

In one embodiment, the present invention provides a method, wherein the method inhibits the production of hydrogen sulfide and/or mercaptans from a liquid within a reservoir defined by a solid silicate surface, the method comprising contacting the solid silicate surface with a catalytically effective amount of the recombinant protein according to some embodiments of the present invention, wherein the recombinant protein catalyzes the oxidation of the hydrogen sulfide and/or mercaptans to a sulfur containing oxidation product.

In one embodiment, the liquid is sour well water.
In one embodiment, the liquid is sea water.
In one embodiment, the liquid is brine.

BRIEF DESCRIPTION OF DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

Figure 1:
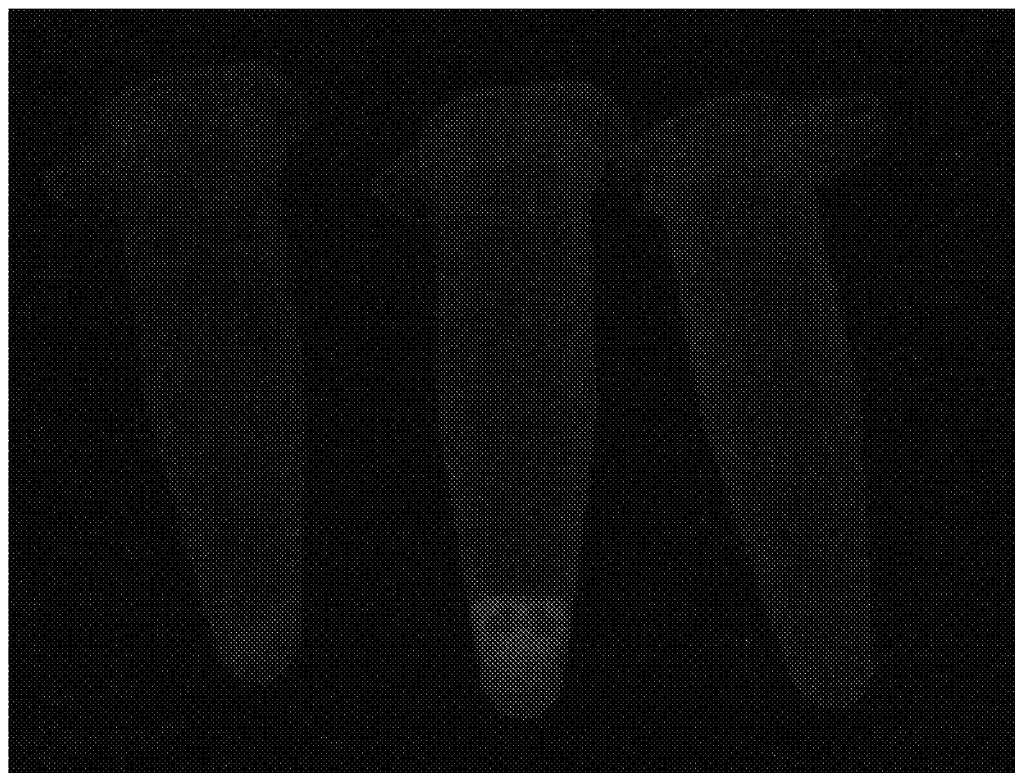
FIG. 1 shows a recombinant protein according to some embodiments of the present invention immobilized onto sand.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the

DETAILED DESCRIPTION

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, throughout the specification, the meaning of "a," "an," and "the" include plural references. The meaning of "in" includes "in" and "on."

As used herein, the term "mercaptan" shall include alkyl mercaptans and thiols of the formula R—SH where R is an unsubstituted or substituted alkyl, thiol carboxylic acids and dithio acids.

As used herein, the term "aqueous substrate" shall refer to any "sour" aqueous substrate, including waste water streams in transit to or from municipal waste water treatment facilities, tanning facilities, and the like.

The term "hydrocarbon substrate" is meant to include unrefined and refined hydrocarbon products, including natural gas, derived from petroleum or from the liquefaction of coal, both of which contain hydrogen sulfide or other sulfur-containing compounds. Thus, particularly for petroleum-based fuels, the term "hydrocarbon substrate" includes, but is not limited to, wellhead condensate as well as crude oil which may be contained in storage facilities at the producing field. "Hydrocarbon substrate" also includes the same materials transported from those facilities by barges, pipelines, tankers, or trucks to refinery storage tanks, or, alternately, transported directly from the producing facilities through pipelines to the refinery storage tanks. The term "hydrocarbon substrate" also includes refined products, interim and final, produced in a refinery, including distillates such as gasoline, distillate fuels, oils, and residual fuels and to vapors produced by the foregoing materials.

Hydrogen Sulfide and/or Mercaptan Scavenging Enzymes According to Some Embodiments of the Present Invention In some embodiments, the present invention provides a recombinant protein comprising an affinity tag configured to attach the recombinant protein to a silicate surface, fused to a hydrogen sulfide scavenging enzyme.

In some embodiments, the hydrogen sulfide scavenging enzyme is a sulfide quinone reductase (SQR) enzyme.

Without intending to be limited to any particular theory, the sulfide quinone reductase (SQR) enzyme prevents the formation of hydrogen sulfide and mercaptans in a liquid within a reservoir. The formation of hydrogen sulfide and/or mercaptans can contribute to corrosion of the materials of the reservoir, and vessels used to transport, store, and/or manufacture the liquid.

In some embodiments, the sulfide quinone reductase (SQR) enzyme may originate from various organisms.

In some embodiments, the SQR enzyme is derived from *Acidophilus ferroxidans*.

In some embodiments, the SQR enzyme may be derived from a gram negative, acidophilic and thermophilic bacterium, such as *Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), or any combination thereof.

In some embodiments, a nucleotide sequence encoding the SQR enzyme may be derived from a gram negative, acidophilic and thermophilic bacterium, such as *Acidithiobacillus ferroxidans*, *Metallospora cuprina* or *Metallospora sedula*, using polymerase chain reaction (PCR) amplification.

In some embodiments, the SQR enzyme is the SQR enzyme disclosed in U.S. Patent Application Publication No. 20160039697 A1, which is incorporated herein by reference in its entirety.

In some embodiments, the sulfide quinone reductase (SQR) enzyme is isolated according to the methods described in U.S. Patent Application Publication No. 20160039697 A1, which is incorporated herein by reference in its entirety.

In some embodiments, the hydrogen sulfide scavenging enzyme is cysteine synthase.

In some embodiments, the cysteine synthase is derived from *Acidithiobacillus caldus* SM-1. Alternatively, in some embodiments, the cysteine synthase is derived from *Aeropyrum pernix*.

In some embodiments, the hydrogen sulfide scavenging enzyme is an enzyme at least 80% homologous to a SQR derived from, e.g., but not limited to, *Acidophilus ferroxidans*, *Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans*, *Metallospora cuprina* or *Metallospora sedula*. In some embodiments, the hydrogen sulfide scavenging enzyme is an enzyme at least 85% homologous to a SQR derived from, e.g., but not limited to, *Acidophilus ferroxidans*, *Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans*, *Metallospora cuprina* or *Metallospora sedula*. In some embodiments, the hydrogen sulfide scavenging enzyme is an enzyme at least 90% homologous to a SQR derived from, e.g., but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*.

In some embodiments, the hydrogen sulfide scavenging enzyme is an enzyme at least 95% homologous to a SQR derived from, e.g., but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme at least 96% homologous to a SQR derived from, e.g., but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme at least 97% homologous to a SQR derived from, e.g., but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme at least 98% homologous to a SQR derived from, e.g., but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme at least 99% homologous to a SQR derived from, e.g., but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*.

In some embodiments, the hydrogen sulfide scavenging enzyme is an enzyme between 80% and 99% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme between 85% and 99% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme between 90% and 99% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme between 95% and 99% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*.

In some embodiments, the hydrogen sulfide scavenging enzyme is an enzyme between 96% and 99% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme between 97% and 99% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme between 98% and 99% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*.

In some embodiments, the hydrogen sulfide scavenging enzyme is an enzyme between 95% and 98% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme between 95% and 97% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithiobacillus ferroxidans, Metallospora cuprina* or *Metallospora sedula*. In some embodiments, the hydrogen sulfide scavenging enzyme is an enzyme between 95% and 96% homologous to a SQR derived from, but not limited to, *Acidophilus ferroxidans, Acidithiobacillus albertensis* (SEQ ID. No: 8), *Thiohalospira halophila* DSM 15071 (SEQ ID. No: 9), endosymbiont of *Riftia pachyptila* (vent Ph05) (SEQ ID. No:10), *Acidovorax soli* (SEQ ID. No:11), *Thiothrix caldifontis* (SEQ ID. No:12), *Acidithobacillus ferroxidans, Metallospora cuprina* or *Metallospora sedula*.

In some embodiments, the hydrogen sulfide scavenging enzyme is an enzyme at least 80% homologous to a SQR enzyme disclosed in U.S. Patent Application Publication No. 20160039697 A1. In some embodiments, the hydrogen sulfide scavenging enzyme is an enzyme at least 85% homologous to a SQR enzyme disclosed in U.S. Patent Application Publication No. 20160039697 A1. In some embodiments, the hydrogen sulfide scavenging enzyme is an enzyme at least 90% homologous to a SQR enzyme disclosed in U.S. Patent Application Publication No. 20160039697 A1. In some embodiments, the hydrogen sulfide scavenging enzyme is an enzyme at least 95% homologous to a SQR enzyme disclosed in U.S. Patent Application Publication No. 20160039697 A1.

In some embodiments, the hydrogen sulfide scavenging enzyme is an enzyme between 80% and 99% homologous to a SQR enzyme disclosed in U.S. Patent Application Publication No. 20160039697 A1. In some embodiments, the hydrogen sulfide scavenging enzyme is an enzyme between 85% and 99% homologous to a SQR enzyme disclosed in U.S. Patent Application Publication No. 20160039697 A1. In some embodiments, the hydrogen sulfide scavenging enzyme is an enzyme between 90% and 99% homologous to a SQR enzyme disclosed in U.S. Patent Application Publication No. 20160039697 A1. In some embodiments, the hydrogen sulfide scavenging enzyme is an enzyme between 95% and 99% homologous to a SQR enzyme disclosed in U.S. Patent Application Publication No. 20160039697 A1.

In some embodiments, the hydrogen sulfide scavenging enzyme is an enzyme between 96% and 99% homologous to a SQR enzyme disclosed in U.S. Patent Application Publication No. 20160039697 A1. In some embodiments, the hydrogen sulfide scavenging enzyme is an enzyme between 97% and 99% homologous to a SQR enzyme disclosed in U.S. Patent Application Publication No. 20160039697 A1. In some embodiments, the hydrogen sulfide scavenging enzyme is an enzyme between 98% and 99% homologous to a SQR enzyme disclosed in U.S. Patent Application Publication No. 20160039697 A1.

In some embodiments, the hydrogen sulfide scavenging enzyme is an enzyme between 95% and 98% homologous to a SQR enzyme disclosed in U.S. Patent Application Publication No. 20160039697 A1. In some embodiments, the hydrogen sulfide scavenging enzyme is an enzyme between 95% and 97% homologous to a SQR enzyme disclosed in U.S. Patent Application Publication No. 20160039697 A1. In some embodiments, the hydrogen sulfide scavenging enzyme is an enzyme between 95% and 96% homologous to a SQR enzyme disclosed in U.S. Patent Application Publication No. 20160039697 A1.

In some embodiments, the hydrogen sulfide scavenging enzyme is an enzyme at least 80% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme at least 85% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme at least 90% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme at least 95% homologous to a cysteine synthase derived from, e.g., but not limited to, *Acidithiobacillus caldus* SM-1 or *Aeropyrum pernix*.

In some embodiments, the hydrogen sulfide scavenging enzyme is an enzyme at least 96% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme at least 97% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme at least 98% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme at least 99% homologous to a cysteine synthase derived from, e.g., but not limited to, *Acidithiobacillus caldus* SM-1 or *Aeropyrum pernix*.

In some embodiments, the hydrogen sulfide scavenging enzyme is an enzyme between 80% and 99% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme between 85% and 99% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme between 90% and 99% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme between 95% and 99% homologous to a cysteine synthase derived from, e.g., but not limited to, *Acidithiobacillus caldus* SM-1 or *Aeropyrum pernix*.

In some embodiments, the hydrogen sulfide scavenging enzyme is an enzyme between 96% and 99% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme between 97% and 99% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme between 98% and 99% homologous to a cysteine synthase derived from, e.g., but not limited to, *Acidithiobacillus caldus* SM-1 or *Aeropyrum pernix*.

In some embodiments, the hydrogen sulfide scavenging enzyme is an enzyme between 95% and 98% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme between 95% and 97% homologous to a cysteine synthase derived from, e.g., but not limited to, *Acidithiobacillus caldus* SM-1 or *Aeropyrum pernix*. In some embodiments, the hydrogen sulfide scavenging enzyme is an enzyme between 95% and 96% homologous to a cysteine synthase derived from, e.g., but not limited to, *Acidithiobacillus caldus* SM-1 or *Aeropyrum pernix*.

Affinity Tags Suitable for Use in the Hydrogen Sulfide and/or Mercaptan Scavenging Enzymes According to Some Embodiments of the Present Invention In some embodiments, the present invention provides a recombinant protein comprising an affinity tag configured to attach the recombinant protein to a silicate surface, fused to a hydrogen sulfide scavenging enzyme.

Without intending to be limited to any particular theory, in some embodiments, the affinity tag has an affinity for silicates. In some embodiments the silicate is the silicate surface of a reservoir, pipe, or storage vessel containing a liquid, thereby enabling a protein, such as, the hydrogen sulfide scavenging enyme, that contains the affinity tag to bind to the silicate surface, such that the protein remains fixed to the silicate surface.

In some embodiments, the affinity tag enables the recombinant protein according to some embodiments of the present invention to remain attached to the silicate surface during any natural or induced flux of the liquid through the reservoir, pipe, or storage vessel.

In some embodiments, the affinity tag is fused to the hydrogen sulfide scavenging enzyme such that the affinity tag does not interfere with the catalytic activity of the hydrogen sulfide scavenging enzyme. Accordingly, in some embodiments, the affinity tag may be attached to the hydrogen sulfide scavenging enzyme via linker.

Factors that may influence the catalytic activity of the hydrogen sulfide scavenging enzyme include, but are not limited to, the relative size of the affinity tag compared to the hydrogen sulfide scavenging enzyme, the distance between the affinity tag and the hydrogen sulfide scavenging enzyme, the relative orientation of the affinity tag and the hydrogen sulfide scavenging enzyme (i.e., if the affinity tag is fused to either the N- or C-terminus of the hydrogen sulfide scavenging enzyme), and the like.

In some embodiments, the affinity tag is fused to the N-terminus of the hydrogen sulfide scavenging enzyme. Alternatively, in some embodiments, the affinity tag is fused to the C-terminus of the hydrogen sulfide scavenging enzyme.

In some embodiments, the affinity tag is incorporated into the hydrogen sulfide scavenging enzyme. In some embodiments, the incorporation orients the active site of the hydrogen sulfide scavenging enzyme away from the silicate surface, thereby reducing stearic hinderance.

In some embodiments, the affinity tag configured to attach the recombinant protein to a silicate surface is nonarginine.

In some embodiments, the affinity tag configured to attach the recombinant protein to a silicate surface is the 30 kDa L2 protein from the *E. Coli* 50S ribosomal subunit.

In some embodiments, the affinity tag is the peptide having the amino acid sequence set forth in SEQ ID. No: 3.

In some embodiments, the affinity tag is the peptide having the amino acid sequence set forth in SEQ ID. No: 4.

In some embodiments, the affinity tag is a polyhistidine. In some embodiments, the polyhistidine tag comprises at least 6 histidine (HIS) residues. In some embodiments, the polyhistidine tag binds to a metal, e.g., but not limited to, a metal comprising nickel.

In some embodiments, the recombinant protein comprising an affinity tag configured to attach the recombinant protein to a silicate surface, fused to a hydrogen sulfide scavenging enzyme comprises the protein having the amino acid sequence set forth in SEQ ID. No: 1.

In some embodiments, the recombinant protein comprising an affinity tag configured to attach the recombinant protein to a silicate surface, fused to a hydrogen sulfide scavenging enzyme comprises the protein having the amino acid sequence set forth in SEQ ID. No: 2.

In some embodiments, the recombinant protein comprising an affinity tag configured to attach the recombinant protein to a silicate surface, fused to a hydrogen sulfide scavenging enzyme is expressed in a bacterial expression system, isolated, purified, and added to the solid silicate surface in a catalytically effective amount. Methods to generate, express, and/or purify recombinant protein using bacterial expression systems are readily selected by one of ordinary skill in the art.

Methods of Scavenging Hydrogen Sulfide and/or Mercaptans According to Some Embodiments of the Present Invention In some embodiments, the present invention provides a method, wherein the method scavenges hydrogen sulfide and/or mercaptans from a liquid within a reservoir defined by a solid silicate surface, the method comprising contacting the solid silicate surface with a catalytically effective amount of the recombinant protein according to some embodiments of the present invention, wherein the recombinant protein catalyzes the oxidation of the hydrogen sulfide and/or mercaptans to a sulfur containing oxidation product.

In some embodiments, the present invention provides a method, wherein the method inhibits the production of hydrogen sulfide and/or mercaptans from a liquid within a reservoir defined by a solid silicate surface, the method comprising contacting the solid silicate surface with a catalytically effective amount of the recombinant protein according to some embodiments of the present invention, wherein the recombinant protein catalyzes the oxidation of the hydrogen sulfide and/or mercaptans to a sulfur containing oxidation product.

Generally, for industrial or commercial use, the recombinant protein according to some embodiments of the present invention may be contacted with a stream containing the hydrogen sulfide or mercaptans for removal, and allowed to attach to the silicate surface enclosing the stream. Contact can occur in a variety of containers, such as a process or transport line, a separate stirred or non-stirred container or other vessels such as scrubbers or strippers. Further, the recombinant protein according to some embodiments of the present invention may be added via surface or downhole equipment or at any time in the process stream in recovering crude oil, and allowed to attach to the silicate surface, so as to remove the noxious quality and corrosive nature of the hydrogen sulfide and mercaptans in the processing system.

The methods according to some embodiments of the present invention have applicability in the removal of hydrogen sulfide and mercaptans of the formula R—SH wherein R is an alkyl group having from 1 to 40 carbon atoms, alternatively from 1 to 20 carbon atoms, alternatively from 1 to 6 carbon. Without intending to be limited by any particular theory, such mercaptans have noxious odors and are corrosive.

The methods defined herein are applicable to a wide variety of fluid streams, including liquefied petroleum gas as well as crude oil and petroleum residual fuel, heating oil, etc. In addition, the method are applicable to gaseous hydrocarbon streams.

In some embodiments, the liquid is water.
In some embodiments, the liquid is sour well water.
In some embodiments, the liquid is a salt water.
In some embodiments, the liquid is sea water.
In some embodiments, the liquid is brine.
In some embodiments, the liquid is not a hydrophobic solvent, e.g., but not limited to, an oil.
In some embodiments, the catalytically effective amount of SQR enzyme is an amount sufficient to effectuate the desired result over a sustained period of time and thus is dependent on the amount of the hydrogen sulfide and/or mercaptan in the medium being treated. In general, the amount of the SQR enzyme added to the medium is at least an effective scavenging amount, for example, from about 0.05 ppm to about 2,000 ppm or more, alternatively from about 20 to about 1,200 ppm, and alternatively from about 100 to about 400 ppm of hydrogen sulfide and/or mercaptan.

Reference is now made to the following examples, which together with the above descriptions illustrate some embodiments of the invention in a non-limiting fashion.

EXAMPLES

Example 1: Binding of the Recombinant Proteins According to Some Embodiments of the Present Invention to Silicate Substrates The sequence for enhanced GFP (eGFP) was used as a model system. The sequence was obtained from the National Center for Biotechnology Information and developed in silico with an endopeptidase cleavage site, a five amino acid linker and a nine arginine repeat on the C-terminal end of the protein. Nde1 and BamH1 restriction endonuclease sites were cloned onto the 5' and 3' ends of the gene, respectively. The sequence was codon optimized, using the methods described in U.S. Pat. No. 8,326,547, which are incorporated by reference herein in their entireties. The sequences was then submitted to Genscript for production and cloning into a pET-11a expression vector from Agilent. Plasmids were transformed into BL21(DE3) T1$^r$ competent cells from Sigmaldrich. Cells were grown in Luria Bertani nutrient medium with 100 μg/mL ampicillin and 0.5 mM IPTG for expression. The codon optimized sequence for eGFP-$R_9$ is set forth in SEQ ID NO: 5. $R_9$ as used herein refers to the nonarginine affinity tag. The translated sequence of the eGFP-$R_9$ is set forth in SEQ ID NO: 6. The amino acids in bold denotes the nonaarginine affinity tag. The "*" of SEQ ID NO: 6 represents the end or "stop" of translation. The "GS" following the "*" represents the amino acids (glycine and serine, respectively) that are included as a translation of the genetic code due to the use of engineered restriction endonuclease sites, but the GS is not part of the translated peptide since the peptide will end coding at the stop codon ("*").

The sequence for L2 was obtained from the National Center for Biotechnology Information. A fusion protein comprising L2 fused to the C-terminus of SQR was generated. The nucleotide sequence for SQR-L2 is set forth in SEQ ID NO: 7. The translated sequence of SQR-L2 is set forth in SEQ ID NO: 2. The amino acids in bold denotes the L2 affinity tag.

Plasmids were transformed into BL21(DE3) T1$^r$ competent cells from Sigm Aldrich. Cells were grown in Luria Bertani nutrient medium with 100 μg/mL ampicillin and 0.5 mM IPTG for expression. Cells were harvested via centrifugation (3,000 RPM for 20 minutes) and the supernatant discarded. Cell pellets were resuspended in dH$_2$O or Tris Buffered Saline (TBS), pH 7.6 at a ratio of 5 volumes of buffer per 1 volume of cell pellet. Cell debris was removed via centrifugation and the clear supernatant kept as the tagged protein.

```
                    Sequence Listings:

SEQ ID NO:   Sequence

1        MAHVVILGGGTGGMPAAYEMKEALGSGHEVTLISANDYFQFVPSNPW
             VGVGWKERDDITFPIRHYVERKGIHFVAQSAERIDAEAQNITLADGS
             TVHYDYLMITAGPKLAFENVPGSDPHEGPVQSICTVDHAERAFAEYQ
             ALLREPGPIAIGAMAGASCFGPAYEYAMIVASDLKKRGMRDKIPSFT
             FITSEPYLGHLGIQGVGDSKGILTKGLKEEGIEAYTNCKVTKVEDNK
             MYVTQVDEKGETIKEMVLPVKLGMMIPAFKGVPAVAGVEGLCNPGGF
             VLVDEHQRSKKYANIFAAGIAIAIPPVETTPVPTGAPKTGYMIESMV
             SAAVHNIKADLEGRKGEQTMGTWNAVCFADMGDRGAAFIALPQLKPR
             KVDVFAYGRWVHLAKVAFEKYFIRKMKIGVSEPPYEKVLFKKMGITR
             LKEEDAHRKASETHANNAHDAVIDRRRRRRRRR

2        MAHVVILGGGTGGMPAAYEMKEALGSGHEVTLISANDYFQFVPSNPW
             VGVGWKERDDITFPIRHYVERKGIHFVAQSAERIDAEAQNITLADGS
             TVHYDYLMITAGPKLAFENVPGSDPHEGPVQSICTVDHAERAFAEYQ
             ALLREPGPIAIGAMAGASCFGPAYEYAMIVASDLKKRGMRDKIPSFT
             FITSEPYLGHLGIQGVGDSKGILTKGLKEEGIEAYTNCKVTKVEDNK
             MYVTQVDEKGETIKEMVLPVKLGMMIPAFKGVPAVAGVEGLCNPGGF
             VLVDEHQRSKKYANIFAAGIAIAIPPVETTPVPTGAPKTGYMIESMV
             SAAVHNIKADLEGRKGEQTMGTWNAVCFADMGDRGAAFIALPQLKPR
             KVDVFAYGRWVHLAKVAFEKYFIRKMKIGVSEPPYEKVLFKKMGITR
             LKEEDAHRKASETHANNAHAVVKCKPTSPGRRHVVKVVNPELHKGKP
             FAPLLEKNSKSGGRNNNGRITTRHIGGGHKQAYRIVDFKRNKDGIPA
             VVERLEYDPNRSANIALVLYKDGERRYILAPKGLKAGDQIQSGVDAA
             IKPGNTLPMRNIPVGSTVHNVEMKPGKGGQLARSAGTYVQIVARDGA
             YVTLRLRSGEMRKVEADCRATLGEVGNAEHMLRVLGKAGAARWRGVR
             PTVRGTAMNPVDHPGGGHEGRNFGKHPVTPWGVQTKGKKTRSNKRTD
             KFIVRRRSK

3        RRRRRRRRR

4        AVVKCKPTSPGRRHVVKVVNPELHKGKPFAPLLEKNSKSGGRNNNGR
             ITTRHIGGGHKQAYRIVDFKRNKDGIPAVVERLEYDPNRSANIALVL
             YKDGERRYILAPKGLKAGDQIQSGVDAAIKPGNTLPMRNIPVGSTVH
             NVEMKPGKGGQLARSAGTYVQIVARDGAYVTLRLRSGEMRKVEADCR
             ATLGEVGNAEHMLRVLGKAGAARWRGVRPTVRGTAMNPVDHPGGGHE
             GRNFGKHPVTPWGVQTKGKKTRSNKRTDKFIVRRRSK
```

| SEQ ID NO: | Sequence |
|---|---|
| 5 | catatggtgagcaaaggcgaagaactgtttaccggcgtggtgccgat<br>tctggtggaactggatg<br>gcgatgtgaacggccatttagcgtgagcggcgaaggcgaaggc<br>gatgcgacctatggcaaactgaccctgaaatttatttgcaccaccgg<br>caaactgccggtgccgtggccgacccTggtgaccaccctgacctatg<br>gcgtgcagtgctttagccgctatccggatcatatgaaacagcatgat<br>tttttttaaaagcgcgatgccggaaggctatgtgcaggaacgcaccat<br>tttttttaaagatgatggcaactataaaacccgcgcggaagtgaaat<br>ttgaaggcgataccctggtgaaccgcattgaactgaaaggcattgat<br>tttaaagaagatggcaacattctgggccataaactggaatataacta<br>taacagccataacgtgtatattatggcggataaacagaaaaacggca<br>ttaaagtgaactttaaaattcgccataacattgaagatggcagcgtg<br>cagctggcggatcattatcagcagaacaccccgattggcgatggccc<br>ggtgctgctgccggataaccattatctgagcacccagagcgcgctga<br>gcaaagatccgaacgaaaaacgcgatcatatggtgctgctggaattt<br>gtgaccgcggcgggcattaccctgggcatggatgaactgtataaaga<br>tgatgatgataaagatgcggtgattgatcgccgccgccgccgccgcc<br>gccgccgctgaggatcc |
| 6 | HMVSKGEELFTGVVPILVELDGDVNGHKFSVSGEGEGDATYGKLTLK<br>FICTTGKLPVPWPTLVTTLTYGVQCFSRYPDHMKQHDFFKSAMPEGY<br>VQERTIFFKDDGNYKTRAEVKFEGDTLVNRIELKGIDFKEDGNILGH<br>KLEYNYNSHNVYIMADKQKNGIKVNFKIRHNIEDGSVQLADHYQQNT<br>PIGDGPVLLPDNHYLSTQSALSKDPNEKRDHMVLLEFVTAAGITLGM<br>DELYKDDDDKDAVIDRRRRRRRR*GS |
| 7 | catatggcgcatgtggtgattctgggcggcggcaccggcggcatgcc<br>ggcggcgtatgaaatgaaagaagcgctgggcagcggccatgaagtga<br>ccctgattagcgcgaacgattattttcagtttgtgccgagcaacccg<br>tgggtgggcgtgggctggaaagaacgcgatgatattacctttccgat<br>tcgccattatgtggaacgcaaaggcattcattttgtggcgcagagcg<br>cggaacgcattgatgcggaagcgcagaacattaccctggcggatggc<br>agcaccgtgcattatgattatctgatgattaccgcgggcccgaaact<br>ggcgtttgaaaacgtgccgggcagcgatccgcatgaaggccggtgc<br>agagcatttgcaccgtggatcatgcggaacgcgcgtttgcggaatat<br>caggcgctgctgcgcgaaccgggcccgattgcgattggcgcgatggc<br>gggcgcgagctgctttggcccggcgtatgaatatgcgatgattgtgg<br>cgagcgatctgaaaaaacgcggcatgcgcgataaaattccgagcttt<br>acctttattaccagcgaacctatctgggccatctgggcattcaggg<br>cgtgggcgatagcaaaggcattctgaccaaaggcctgaaagaagaag<br>gcattgaagcgtataccaactgcaaagtgaccaaagtggaagataac<br>aaaatgtatgtgacccaggtggatgaaaaaggcgaaaccattaaaga<br>aatggtgctgccggtgaaactgggcatgatgattccggcgtttaagg<br>gcgtgccggcggtggcgggcgtggaaggcctgtgcaacccgggcggc<br>tttgtgctggtggatgaacatcagcgcagcaaaaaaatgcgaacat<br>ttttgcggcgggcattgcgattgcgattccgccggtggaaaccaccc<br>cggtgccgaccggcgcgccgaaaaccggctatatgattgaaagcatg<br>gtgagcgcggcggtgcataacattaaagcggatctggaaggccgcaa<br>aggcgaacagaccatgggcacctggaacgcggtgtgctttgcggata<br>tgggcgatcgcggcgcggcgtttattgcgctgccgcagctgaaaccg<br>cgcaaagtggatgtgtttgcgtatggccgctgggtgcatctggcgaa<br>agtggcgtttgaaaaatattttattcgcaaaatgaaaattggcgtga<br>gcgaaccgtttatgaaaaagtgctgtttaaaatgatgggcattacc<br>cgcctgaaagaagaagatgcgcatcgcaaagcgagcgaaacccatgc<br>gaacaacgcgcatgcgcgtggtgaaatgcaaaccgaccagcccgggcc<br>gccgccatgtggtgaaagtggtgaacccggaactgcataaaggcaaa<br>ccgtttgcgccgctgctggaaaaaaacagcaaaagcggcggccgcaa<br>caacaacggccgcattaccacccgccatattggcggcggccataaac<br>aggcgtatcgcattgtggattttaaacgcaacaaagatggcattccg<br>gcggtggtggaacgcctggaatatgatccgaaccgcagcgcgaacat<br>tgcgctggtgctgtataaagatggcgaacgccgctatattctggcgc<br>cgaaaggcctgaaagcgggcgatcagattcagagcggcgtggatgcg<br>gcgattaaaccgggcaacaccctgccgatgcgcaacattccggtggg<br>cagccaccgtgcataacgtggaaatgaaaccgggcaaaggcggccagc<br>tggcgcgcagcgcgggcacctatgtgcagattgtggcgcgcgatggc<br>gcgtatgtgaccctgcgcctgcgcagcggcgaaatgcgcaaagtgga<br>agcggattccgcgcgaccctgggcgaagtgggcaacgcggaacata<br>tgctgcgcgtgctgggcaaagcgggcgcggcgctggcgcggcgtg<br>cgcccgaccgtgcgcggcaccgcgatgaacccggtggatcatccggg<br>cggcggccatgaaggccgcaactttggcaaacatccggtgaccccgt<br>ggggcgtgcagaccaaaggcaaaaaacccgcagcaacaaacgcacc<br>gataaatttattgtgcgccgccgcagcaaatgaggatcc |
| 8 | MAHVVILGAGTGGMPAAYEMKEALGSGHEVTLISANDYFQFVPSNPW<br>VGVGWTKRDDIAFPIKPYVERKGIHFIPKAAEKIDAEGQEITLADGS |

Sequence Listings:

| SEQ ID NO: | Sequence |
|---|---|
|  | KVRYDYLLITTGPKLAFENVPGSDPHEGPIQSICTVDHAEKAYHDYQ<br>ALLAEPGPIVIGAMGGASCFGPAYEYAMVVASDLKKRGMRDKISSFT<br>FVTSEPYLGHLGIQGVGDSTGILSKGLKEEGIEAYTNCKVTKVEGGK<br>MFVTQVNDKGEVAKEFTLPVKFGMMIPAFKGVPAVAGVEGLCNPGGF<br>VLVDEHQRSKKYANIFAAGIAIAIPPVEATPVPTGAPKTGYMIESMV<br>SAAVHNIKADLEGRKGEQTMGTWNAVCFADMGDRGAAFVALPQLRPR<br>KVDVFAYGRWVHLAKVAFEKYFIRKMKMGVSEPFYEKVLFKKMGITR<br>LKEEVPPHRKAS |
| 9 | MAHIVILGAGTGGTPAAYEMREALGREHKVTLINASETFQFVPSNPW<br>VAVGWRERDDTTFPLRQYVEKKGINFIADRVDRIDPEANQLTLAGGD<br>TVDYDYLVLTTGPMLAFDEVEGTGPHDGYTQSVCTIDHAETAYQKYE<br>EFLKNPGPVVVGAVQGASCFGPAYEFAMILDRDLRKRKMRDQVPITF<br>VTSEPYIGHMGLGGVGDSKGLLEHELRERHINWITNARTERVEDGKM<br>YVTQLDEKGEVLKEHELDFNYSMMLPAFRGVPAVADVEGLCNPRGFV<br>KVDECQRSPAYSNIFAAGVGIAIPPVEQTTVATGAPKTGYMIESMVT<br>AIVENIAGEVEGKGGCNTQGTWSTICLADLGDTGAAFVALPQIPPRN<br>VTWSKKGKWVHYAKIAFEKYFMRKMKTGHSEPIYEKYVLRMLGINRL<br>KK |
| 10 | MAHVVVLGAGTGGMPCAYELRAELGREHEVTMINEREYFQFVPSNPW<br>LAVGWRDRSHITFDIRPHLERKGINFIAKRVDKIDAEGNKLELDDGE<br>TIEYDYLVIATGPRLAFEEVEGSGPEGHTQSICTVNHAEKAFDAYKD<br>LLDEPGPVIIGAMPFASCFGPAYEFSFIMDSDLRKRKMRDKVPMTYV<br>TSEPYIGHLGLGGVGDSKGFLESDFRAHHINWITNAKVIKVEAGKMF<br>VEQYDDSGHKIKEHELEFKYSMMLPAFKGVDAVANVEGLCNPRGFVF<br>VDDHQCNPTYKNIYAAGVCIAIPPVEATAVPTGAPKTGYMIESMVTA<br>IVHNIADDLAGKEGTTLATWNAICLADMGDTGAAFVALPQIPPRNVA<br>WFKKGKWVHMAKIAFEKYFIRKMKKGTSEPIYEKYILKMLGIGKLK |
| 11 | MAHIVVIGAGIGGMPAAYELRSKLPAQHRVTVISAVDYFHFVPSNPW<br>IAVGWRQREDIVLQLAPLLQRKGIDFIASPVQTIDAAGNSLALANGQ<br>TVAYDYLVITTGPRLAFEEVPGAGPIDGHTHSICTVDHAQHFWADYE<br>KFLENPGPMVIGAMPGASCFGPAYEFAFIVSADLRKRKLRHKVPLTY<br>VTSEPYIGHLGLGGVGDSKSMLESELRGQDIKWITNAKTTRVEDGKM<br>MVDQLDDQGKLLKQHELPFKLSMMLPAFKGVDAVAAVPSLCNPRGFV<br>LIDAHQRSKAYPNIFAAGVCVAIPPVEVTPVPTGAPKTGYMIETMVS<br>AIVHNIAADLEGKPATATATWNAICLADMGDTGAAFVALPQIPPRNV<br>NWFKKGKWVHLGKIAFEKYFLGKIKSGNTDPIYEKYVLKILGIERLP<br>EPSGPR |
| 12 | MAHIVILGAGTGGMPAAYEMKEMLGKGHEVTVVNERDYFQFVPSNPW<br>VAVGWRTRSDITFPIEKYLSKKDIKFICSRCEKIDAEGNALHLADGQ<br>IVKYDYLVIATGPKLFFQEVEGAGPHGGHTHSVCDVTHAEGAYADYQ<br>KLLAKGSGHIIVGAMPFASCFGPAYEFAFIVDADLRKRGLRHKFKMT<br>YVSSEPYIGHLGLGGVGDSKGMLESELRNHHMGWITNAKTTKVEAGK<br>MHVTEMTAKGEVEKEHVIDFDMAMMLPAFKGVDAVAAVEGLCNPRGF<br>VIVDELHRSPKYKNIYSAGVCIAIPPVEATPVPTGAPKTGYMIESMV<br>TSLVHNIADELAGKEPHTTATWNAICLADMGDTGAAFVALPQIPPRN<br>VAWFKKGKWVHMAKIAFEKYFIRKMKKGSSEPFYEKSILKMMGITRI | eGFP-R$_9$ proteins were mixed with sand, sandstone wafers, glass beads or glass slides and visualized in a dark room with ultraviolet light (360 nm). A green emission indicates the presence of GFP. The tagged protein contacted the substrate at 37° C. for at least an hour. Samples were then removed from the protein fluid and washed with at least 10 volumes of dH$_2$O and then visualized at 360 nM. As shown in FIG. 1, the tagged eGFP fluoresces brightly. The sample vials on the left and in the middle have eGFP-R$_9$ tagged sand. The sand in the tube on the left has been washed with 50 sample volumes of dH$_2$O. The tube in the middle has not been washed. The tube on the left fluoresces under these conditions indicating the presence of GFP. The tube on the right contains moist sand without eGFP.

Figure 2:
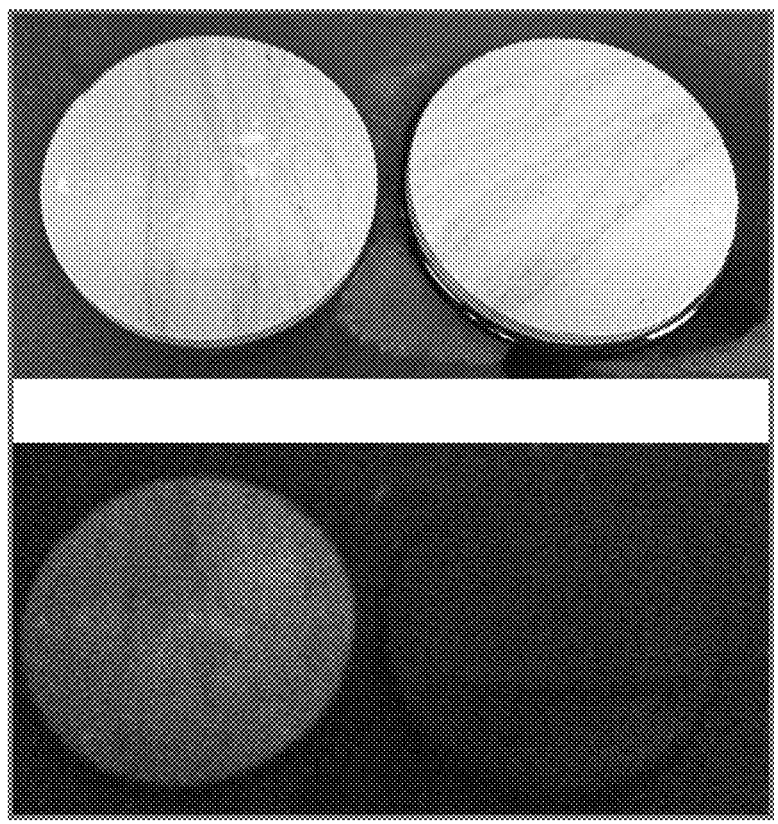
FIG. 2 shows a recombinant protein according to some embodiments of the present invention immobilized onto sandstone wafers.

Referring to FIG. 2, the image at the top shows the sandstone wafers in natural light. The image at the bottom was taken in ultraviolet light (360 nM). The sandstone wafer on the left was stained for 1 hour at room temperature with eGFP-R9 and then washed with 100 sample volumes of distilled water (dH2O). The wafer on the right was saturated with dH2O only. This indicates that the tag was effective in binding the protein to the wafer. Interestingly, this wafer still fluoresced after drying. Even after 4 weeks of being dry, this wafer still displayed a strong fluorescent signal.

Figure 3:
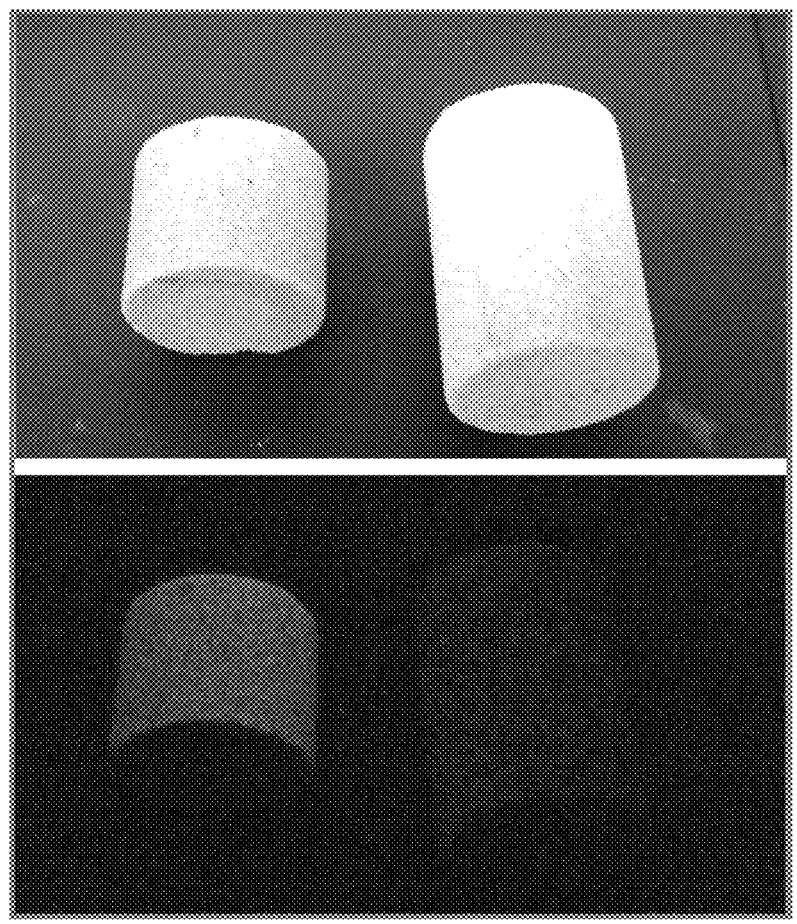
FIG. 3 shows a recombinant protein according to some embodiments of the present invention immobilized onto sandstone cores.

Referring to FIG. 3, the experiment was similar to FIG. 2 except that sandstone cores were used. The treated sample (left) fluoresces strongly in the presence of ultraviolet light. This sandstone core was exposed to eGFP-R$_9$ for 1 hour at room temperature and then washed with 80 core volumes of dH$_2$O.

The eGFP-R$_9$ fusion produced the most conclusive results in these tests. In contrast, it was difficult to produce results with the SQR-L2 enzyme system because the sulfide in solution readily reacted with the sand, wafers and proppant. For example, tests routinely produced false negatives (and sometimes positives) as it was difficult to get a reproducible result with sulfides and solid supports. On average, there were fewer sulfides detected in enzyme treated samples than blank samples, indicating that the enzyme was present and active. We further performed experiments in aqueous solution without the solid substrate present. The goal of the test was to determine if the presence of the 30 KDa tag abolished the enzyme's activity. SQR-L2 was suspended in Tris buffered Saline, pH7.6 and the applied to solutions containing 200 ppm sodium sulfide. Enzymes were allowed to react with the sulfide for 2 hours at room temperature and then the sulfide concentration measured with the HACH HS-C filter paper method from HACH, Colorado. A stock solution of 200 ppm sodium sulfide was used as a sulfide source. A black test paper indicated the presence of sulfide. Therefore, the presence of the active SQR enzyme was shown by an unreacted test paper. As an alternative test, the HACH sulfide test kit was used. The same 200 ppm stock solution of sodium sulfide was used and the presence of sulfide was indicated by the formation of methylene blue (blue color) in liquid samples. Quantification of enzyme activity could be measured by using absorbance at 650 nm. Enzyme treated samples contained 2 mg/L sulfide while the untreated sample was measured off the charts at ≥5 mg/L of sulfide. This indicated that the enzyme was present and functional and that the affinity tag did not abolish the activity of the enzyme.

The $R_9$ and L2 tags do not abolish the activity of the enzymes and the $R_9$ tag clearly adheres to the silicate surfaces as evidenced by the strong fluorescence reporting of the treated samples. Even when the samples are washed, the protein remains affixed to the silicate surfaces. While it was more difficult to measure the efficacy of the SQR-L2 fusion, results clearly indicated that the enzyme was present and functional.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method, wherein the method inhibits the production of hydrogen sulfide, mercaptans, or any combination thereof, from a liquid within a reservoir defined by a solid silicate surface, the method comprising contacting the solid silicate surface with a catalytically effective amount of a recombinant protein, wherein the recombinant protein catalyzes the oxidation of the hydrogen sulfide, mercaptans, or any combination thereof, to a sulfur containing oxidation product, and wherein the recombinant protein comprises an affinity tag configured to attach the recombinant protein to a silicate surface, fused to a hydrogen sulfide scavenging enzyme, and wherein the recombinant protein comprises the protein having the amino acid sequence set forth in SEQ ID NO: 1.

2. The method of claim 1, wherein the liquid is sour well water.

3. The method of claim 1, wherein the liquid is sea water.

4. The method of claim 1, wherein the liquid is brine.

* * * * *